United States Patent [19]

Daum et al.

[11] 3,982,996

[45] Sept. 28, 1976

[54] PROCESS FOR PREPARING AMINOCYCLITOL ANTIBIOTICS

[75] Inventors: Sol J. Daum, Albany; Robert L. Clarke, Bethlehem, both of N.Y.

[73] Assignee: Sterling Drug Inc., New York, N.Y.

[22] Filed: Sept. 22, 1975

[21] Appl. No.: 615,593

[52] U.S. Cl. .................................. 195/29; 195/96
[51] Int. Cl.$^2$ ................................... C12D 9/20
[58] Field of Search .................. 195/96, 80 R, 29

[56] References Cited
UNITED STATES PATENTS 3,541,078  11/1970  Woo et al. ............................ 195/96
3,669,838  6/1972  Shier et al. ............................ 195/96

*Primary Examiner*—Alvin E. Tanenholtz
*Attorney, Agent, or Firm*—William G. Webb; B. W. Wyatt

[57] ABSTRACT

Aminocyclitol antibiotics of the streptamine, deoxystreptamine or dideoxystreptamine type are prepared by culturing a nutrient medium containing carbohydrates, a source of assimilable nitrogen, essential salts and a non-nitrogen containing cyclitol with a mutant of an aminocyclitol antibiotic producing organism.

12 Claims, No Drawings

PROCESS FOR PREPARING AMINOCYCLITOL ANTIBIOTICS

BACKGROUND OF THE INVENTION a. Field of the Invention

This invention relates to a process for preparing aminocyclitol antibiotics of the streptamine, deoxystreptamine or dideoxystreptamine type.

b. Description of the Prior Art

It is known that certain aminocyclitol type antibiotics can be prepared by culturing microorganism mutants in a medium containing carbohydrates, a source of assimilable nitrogen, essential salts and an aminocyclitol subunit, for example streptamine or epistreptamine (Shier et al. U.S. Pat. Nos. 3,669,838, patented June 13, 1972, and 3,833,556, patented Sept. 3, 1974).

SUMMARY OF THE INVENTION

This invention relates, in one process aspect, to a process for preparing aminocyclitol antibiotics of the streptamine, deoxystreptamine or dideoxystreptamine type comprising culturing a nutrient medium containing carbohydrates, a source of assimilable nitrogen, essential salts and a cyclitol of the 2-$R_2'$-5-$R_5'$-3,4,6-trihydroxycyclohexanone, 2-$R_2'$-5-$R_5'$-1,3,4,6-tetrahydroxycyclohexane, or 5-$R_5'$-3,4,6,trihydroxycyclohexene class, or polyacetate esters thereof, in the presence of microorganism mutants which are only capable of biosynthesizing antibiotics of the streptamine, deoxystreptamine or dideoxystreptamine type in the presence of the said cyclitols.

In another process aspect, the invention relates to a process for preparing aminocyclitol antibiotics of the gentamicin type comprising culturing a nutrient medium containing carbohydrates, a source of assimilable nitrogen, essential salts and an aminocyclitol or Schiff base thereof in the presence of a microorganism mutant which is incapable of biosynthesizing the aminocyclitol or Schiff base thereof but which is capable of incorporating the aminocyclitol or Schiff base thereof into the antibiotic molecule as an aminocyclitol unit.

DETAILED DESCRIPTION INCLUSIVE OF THE PREFERRED EMBODIMENTS

Studies with radiolabelled compounds have demonstrated that non-nitrogen containing cyclitols are probable biogenetic precursors of aminocyclitols, such as streptamine and deoxystreptamine [Rinehart et al., J. Am. Chem. Soc. 96, 2263–2265 (1974); Walker et al., Biochem. 8. 763–770 (1969); Demain et al., Bacteriol. Rev. 34, 1–19 (1970)]. Nevertheless, although it is known that aminocyclitols can be incorporated into aminocyclitol antibiotics either by culture of a nutrient medium lacking the aminocyclitol subunit as such and in the presence of an appropriate microorganism [e.g. the incorporation of deoxystreptamine into neomycin by Waksman et al., Science 109, 305–307 (1949)] or by culture of a nutrient medium containing an aminocyclitol subunit in the presence of a microorganism mutant which is incapable of biosynthesizing the aminocyclitol as such but which is capable of incorporating the aminocyclitol into the antibiotic [e.g. the incorporation of streptamine or epistreptamine into the hybrimicin antibiotics by Shier and Rinehart, U.S. Pat. No. 3,669,838, patented June 13, 1972], the direct incorporation of cyclitols into aminocyclitol antibiotics has not been heretofore achieved. In fact, efforts to incorporate either myo-inositol, a probable biogenetic precursor of streptamine, or a hexahydroxy cyclohexane monomethyl ether (quebrachitol) into aminocyclitol antibiotics using the Rinehart/Shier method were completely unsuccessful [Testa et. al., J. Antibiotics 27, 917–921 (1974)].

Yet a process that would permit the use of cyclitols, instead of aminocyclitols, for incorporation into aminocyclitol-type antibiotics by microorganism mutants using the Rinehart/Shier method would provide a very significant advance in the aminocyclitol antibiotic art, because the method would afford, by judicious selection of the microorganism and the cyclitol subunit, a certain degree of biogenetic "tailoring" of the resultant antibiotic molecule. Moreover, since the aminocyclitols are invariably much more expensive than the non-aminated cyclitols, significant savings in costs of the final products could be realized. (For example, streptamine, at present prices, costs about $1 per gram, whereas its probable biogenetic precursor, scyllo-inosose, can be obtained in about 80% yield by fermentative oxydation of myo-inositol, which only costs about 2 cents per gram at present).

It has now been surprisingly found that aminocyclitol antibiotics of the streptamine, deoxystreptamine or dideoxystreptamine type can be produced by culturing a nutrient medium containing carbohydrates, a source of assimilable nitrogen, essential salts and a cyclitol of the 2-$R_2'$-5-$R_5'$-3,4,6-trihydroxycyclohexanone or 2-$R_2'$-5-$R_5'$-1,3,4,6-tetrahydroxycyclohexane class represented by the formula:

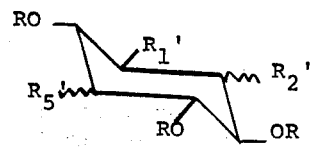

IIa or of the 5-$R_5'$-3,4,6-trihydroxycyclohexene class represented by the formula:

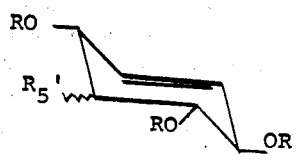

IIb where, in either case, R is hydrogen or acetyl; $R_1'$ is oxo (=O) or hydroxy; and $R_2'$ and $R_5'$ each are hydrogen, hydroxy or OR, in the presence of mutants of organisms which are only capable of biosynthesizing antibiotics of the streptamine, deoxystreptamine or dideoxystreptamine type in the presence of the said cyclitols.

Illustrative aminocyclitol antibiotics which can be obtained by the present process, and the organisms whose mutants are used to produce them, are represented by the following types:

| Antibiotic | Microorganism |
|---|---|
| hybrimicin | Streptomyces fradiae |
| gentamicin | Micromonospora purpurea and Micromonospora echinospora |
| tobramicin | Streptomyces tenebrarius |
| ribostamicin | Streptomyces ribosidificus |
| sisomicin | Micromonospora inyoensis |
| kanamicin | Streptomyces kanamyceticus |
| butirosin | Bacillus circulans |

A preferred aspect of the invention relates to the process for preparing gentamicin-type antibiotics having the formula:

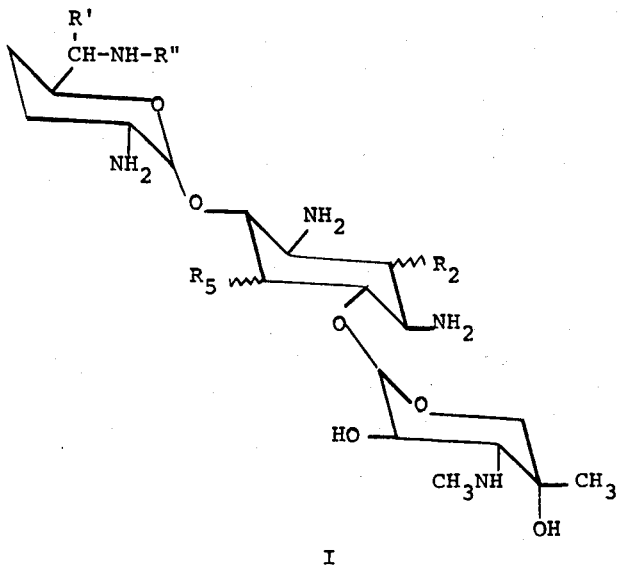

I where R' and R'' each represent hydrogen or methyl, and $R_2$ and $R_5$ each represent hydrogen or hydroxy, which comprises culturing a nutrient medium containing carbohydrates, a source of assimilable nitrogen, essential salts and a cyclitol having one of the formulas IIa or IIb above in the presence of a mutant of *M. purpurea*, namely *M. purpurea* ATCC 31164, which is incapable of biosynthesizing the cyclitol unit but which is capable of incorporating the cyclitol into the antibiotic molecule as an aminocyclitol unit.

It is also significant that the same mutant, *M. purpurea* ATCC 31164, is also capable of incorporating into the antibiotics of formula I above an aminocyclitol having the formula:

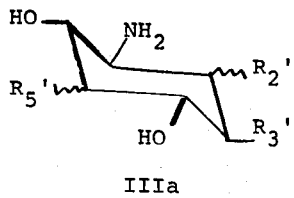

IIIa where $R_2'$ and $R_5'$ are each hydrogen or hydroxy and $R_3'$ is amino or hydroxy, or Schiff bases of the compounds of formula IIIa, for example Schiff bases of benzaldehyde and the aminocyclitols of formula IIIa, and having the formula:

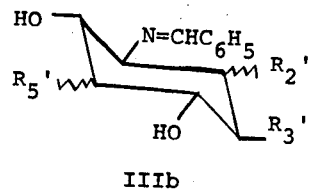

IIIb where $R_3'$ is hydroxy or benzylideneimino ($C_6H_5CH=N$), and $R_2'$ and $R_5'$ have the same meanings as in formula IIIa. The process is carried out in the presence of *M. purpurea* ATCC 31164 using the procedure described above, and comprises culturing a nutrient medium containing carbohydrates, a source of assimilable nitrogen, essential salts and an aminocyclitol having the formula IIIa or IIIb in the presence of *M. purpurea* ATCC 31164. This process is considered to be within the purview of the present invention.

As described in our copending application Ser. No. 550,273, filed Feb. 18, 1975, the compounds of formula I above are produced by culturing a nutrient medium containing carbohydrates, a source of assimilable nitrogen, essential salts and an aminocyclitol having the formula IIIa above where $R_2'$ is hydrogen or hydroxy; $R_3'$ is amino; and $R_5'$ is hydrogen, hydroxy or halogen, in the presence of the microorganism mutant, *Micromonospora purpurea* ATCC 31119. However as indicated above, the aminocyclitols required as substrates in that process are generally rather expensive, and thus the cost of the final products produced is correspondingly high. The present process comprising use of cyclitols for incorporation into aminocyclitol antibiotics thus provides an advantage over the process of the prior invention.

In either case, whether the non-nitrogen containing cyclitols of formulas IIa or IIb or the aminocyclitols of formula IIIa or IIIb are used as substrates, the compounds of formula I are prepared by culturing a nutrient medium containing carbohydrates, a source of nitrogen, essential salts and an added cyclitol of formulas IIa or IIb or an aminocyclitol of formulas IIIa or IIIb in the presence of the mutant, *M. purpurea* ATCC 31164, and isolating the product from the culture medium.

As disclosed in application Ser. No 550,273, the compounds of formula I herein have been tested in a standard serial dilution antibacterial test and have been found to have antibacterial activity, particularly against gentamicin resistant organisms, and such disclosure, together with the biological test data recorded therein, are incorporated herein by reference.

The compounds of formula I are primarily intended for oral, topical or parenteral administration and can be prepared for use by suspension, either in the form of their free bases or as pharmaceutically acceptable, non-toxic acid-addition salts, in an inert carrier such as polyethyleneglycol, or by tabletting or encapsulation for oral administration either alone or with suitable adjuvants, or alternatively they can be formulated with conventional creams or jellies for topical application.

The molecular structures of the compounds of the invention were assigned on the basis of study of their chromatographic characteristics determined by thin layer chromatographic (tlc) analysis; their nuclear magnetic resonance (nmr) and mass spectra; by degradation to known compounds; by comparison with the products prepared by fermentation with mutant *M. purpurea* ATCC 31119 described in our copending application Ser. No. 550,273 using aminocyclitols of formula IIIa as substrates; and by the correspondence between calculated and found values for elementary analyses for the elements.

The following specific examples are illustrative of the manner of carrying out the process of the invention without the latter being limited thereto.

MUTATION PROCESS

In the following procedures, various media constituted as follows were employed.

| Medium 1: | N-Z Amine | |
|---|---|---|
| | | g./l. |
| | Glucose | 10 |
| | Soluble starch | 20 |
| | Yeast extract | 5 |
| | N-Z-Amine-Type A (Difco) | 5 |
| | CaCO$_3$ | 1 |
| | Agar | 15 |
| Medium 2: | Germination Medium (in distilled water) | |
| | Beef extract | 0.3% |
| | Tryptone | 0.5% |
| | Dextrose | 0.1% |
| | Soluble starch | 2.4% |
| | Yeast extract | 0.5% |
| | CaCO$_3$ | 0.4% |
| Medium 3: | TGE | |
| | | g./l. |
| | Trypticase glucose extract | 5.0 |
| | Trypticase peptone | 3.0 |
| | Glucose | 1.0 |
| | Agar | 15.0 |
| Medium 4: | Production Medium | |
| | Beef extract | 0.3% |
| | Yeast extract | 0.5% |
| | Soybean meal | 0.5% |
| | Maltose | 0.1% |
| | Starch | 2.4% |
| | Casamino acid | 0.1% |
| | CaCO$_3$ | 0.4% |
| | CoCl$_2$.6H$_2$O | 1 mg./liter |
| Medium 5: | Streptomicin Assay Agar | |
| | | g./l. |
| | Beef extract | 1.5 |
| | Yeast extract | 3.0 |
| | Peptone | 6.0 |

-continued

| Agar | 15.0 |
|---|---|

The organism *Micromonospora purpurea* ATCC 31119, whose isolation from mutation of the parent organism obtained from the U.S. Department of Agriculture as NRRL 2953 is described in copending application Ser. No. 550,273, was maintained on N-Z amine slants (medium 1). Submerged fermentations were conducted in flasks containing germination medium 2 for 4 days at 37°C. on a rotary shaker. From this first stage seed, a 10% inoculum was transferred to the germination medium (medium 2), and fermentation was continued as above at 28°C. for 7 days.

For purposes of mutating the organism, broth cultures were cultivated in medium 2 (37°C. for 3 days) and the resultant cells harvested by centrifugation, washed and resuspended in buffered saline. This suspension was treated with the mutagenic agent, N-methyl-N-'-nitro-N-nitrosoguanidine. Samples of the mutagenized culture were plated in medium 3 at 37°C. until colonies were evident (usually about one week). Colonies were picked to duplicate plates containing streptomicin assay agar (medium 5).

One set served as a master plate for later recovery while the second set contained 25 μg./ml. of streptamine sulfate and an overlay spore suspension of *B. subtilis* as a challenge test organism. These plates were incubated at 37°C. for 24 hours and examined for zones of inhibition. Those showing the largest zones were transferred from the master plate onto N-Z amine slants (medium 1) and incubated for 1 week at 37°C.

Those mutants incorporating low levels of streptamine sulfate were then screened with streptamine and scyllo-inosose at 500 μg./ml. as base. Stock cultures were transferred to flasks containing medium 2 plus the above intermediates and incubated at 37°C. on a rotary shaker for 7 days. Flasks were periodically assayed for antibiotic activity via the disc diffusion assay method using *B. subtilis* as test organism. Isolates showing zones of inhibition surrounding the disc were designated as streptamine or scyllo-inosose mutants. One such mutant, coded mutant VIB-3P and deposited with the American Type Culture Collection, 12301 Parklawn Drive, Rockville, Md. 20851 as *Micromonospora purpurea* ATCC 31164, was used for the production of the aminocyclitol antibiotics of the streptamine, deoxystreptamine and dideoxystreptamine-type as described below.

PREPARATION OF NOVEL INTERMEDIATES

Preparation 1 dl-Viboquercitol [dl-1,2,3,4,5-cyclohexanepentol (1,2,4-cis)] [McCasland et al., J. Am. Chem. Soc. 75, 4020 (1953)] (0.40 mole) was subjected to microbiological oxidation by *Acetobacter suboxydans* using the procedure described by Posternak, Helv. Chim. Acta 33, 1594–1596 (1950). To the resulting broth was added 5 g. of lead acetate in 60 ml. of water, the solution was filtered through filter aid, and the filtrate was passed over 180 g. of Dowex resin 50–124. The resulting eluate was concentrated to a volume of about 150 ml., diluted with an equal volume of ethanol and cooled. The material which separated was collected to give 15.1 g. of dl-deoxyinosose [dl-2,3,4,5-tetrahydroxy-1-cyclohexanone (2,4-cis)], m.p. 221°–222°C. Further concentration of the filtrate from the first crop afforded three additional crops totaling 28.7 g., m.p. 220°–221°C.

Preparation 2

A solution of 4.5 g. (0.031 mole) of 2,5-dideoxystreptamine in 20 ml. of benzaldehyde was warmed on a stream bath, and the mixture was flushed with nitrogen and set aside for about eight hours. The solution was then diluted with 150 ml. of benzene, cooled, and the solid which separated was collected and dried to give 8.5 g. of crude product which was recrystallized from acetonitrile to give 4.23 g. of 4,6-bis-(benzylideneamino)-1,3-cyclohexanediol (1,3-cis), m.p. 151°–154°C.

Preparation 3

A solution of 9.5 g. (0.053 mole) of dl-epi-inosose [Posternak, Helv. Chim. Acta 19, 1333 (1936)] in 300 ml. of 0.1N hydrochloric acid was reduced with hydrogen over 6 g. of platinum oxide at an initial hydrogen pressure of about 56 p.s.i. The product was isolated by filtration of the reaction mixture, concentration of the filtrate to dryness and recrystallization of the residue from aqueous methanol. There was thus obtained dl-epi-quercitol, m.p. 214°–215°C.

The latter was subjected to microbiological oxidation by *Acetobacter suboxydans* using the procedure described by Posternak recorded above in Preparation 1, and the product was isolated as described in Preparation 1 and recrystallized from ethanol to give dl-2,3,4,6-tetrahydroxy-1-cyclohexanone (2,4,6-cis), m.p. 175°–177°C.

Preparation 4

To a solution of 22.5 g. (0.11 mole) of 3-chloroperbenzoic acid in 150 ml. of methylene dichloride was added 11.4 g. (0.1 mole) of 4-cyclohexene-1α,2β-diol [McCasland et al., J. Org. Chem. 28, 898 (1963)], and the resulting solution was stirred with cooling while maintaining the temperature below 30°C. The mixture was stirred for one hour, diluted with 150 ml. of diethyl ether, stirred for another three hours, and then diluted with 150 ml. of water. The product was isolated from the organic layer in the conventional manner to give 9.1 g. of crude material which was recrystallized from ethanol/ether to give two crops totalling 4.75 g. of 4,5-epoxycyclohexane-1α,2β-diol, m.p. 80°C. and 70°–75°C.

A solution of 6.63 g. (0.051 mole) of the latter in 20 ml. of dimethylsulfoxide was treated with 0.06 ml. of boron trifluoride etherate. The resulting solution was heated on a stream bath for about 20 hours, an additional 0.03 ml. of boron trifluoride etherate added, and the solvent removed in vacuo. The residue was treated with 50 ml. of ethanol, the resulting solid separated, and the filtrate concentrated to dryness to give 7.75 g. of reddish brown oil, 1.1 g. of which was chromatographed on silica gel plates, eluting with tetrahydrofuran, to give 550 mg. of 2,4,5-trihydroxycyclohexanone (2,4-cis) whose mass spectrum gave mass peaks at 144 and 145 and whose infrared spectrum showed a strong peak at 1723 cm$^{-1}$.

BIOSYNTHESES

A. Incorporation of cyclitols

Example 1

The mutant organism, *M. purpurea* ATCC 31164, was maintained on N-Z amine agar slants (medium 1), and a first stage seed was prepared by inoculating a loopfull from the slant to 50 ml. of germination medium (medium 2) and allowed to incubate for four days on a rotary shaker at 27°–28°C. A 5% inoculum was then transferred to 500 ml. of germination medium, and this was incubated for three days as above. One liter of this second stage seed was used to inoculate nine liters of production medium (medium 4) in tanks agitated at 400 r.p.m. and sparged with filtered air at 5 liters/minute at 28°–29°C. for 48 hours. Finally the growth from this third stage seed was used to inoculate seventy liters of production medium containing 16 g. of scyllo-inosose. Fermentation was carried out for four days, agitating at 400 r.p.m. and aerating at 1.5 cubic feet per minute at 29°–30°C.

The tank contents were acidified to pH 2.0 with 10N sulfuric acid and filtered through filter aid to remove mycelia. The filtrate was adjusted to pH 6.0 and passed over an 8 × 50 cm. cation exchange resin bed (Bio-Rex 70, sodium ion form, 20–50 mesh). The eluate was checked for antibiotic activity via bio-assay and found to be inactive against *B. subtilis*. The column was then eluted with 2N sulfuric acid, and 500 ml. fractions were collected. The fractions were bio-assayed as above against *B. subtilis*, and all fractions displaying antibiotic activity were combined and neutralized to give a final volume of 10 liters. This was concentrated to about 5 liters under vacuum, the pH was adjusted to 10.5 with 10N sodium hydroxide, and five volumes of acetone were added with vigorous agitation. The inorganic salts which had separated were removed by filtration, and the filtrate was concentrated in vacuo after adjusting to pH 7.0 with dilute sulfuric acid. When the volume was about 4 liters, the pH was readjusted to 4.5, and the sample was further concentrated to 150 ml. The pH was then adjusted to 10.5, and five volumes of acetone were added for an additional desalting step as described above. The filtrate was concentrated, adjusted to pH 4.5 and further concentrated to 10 ml. On addition of 100 ml. of methanol, a crude antibiotic solid was obtained weighing 9 g., which was dissolved in 10 ml. of water and extracted with five 50 ml. portions of the lower phase of a solvent composed by volume of chloroform (2):isopropanol (1):17% ammonium hydroxide (1). The extracts from two such runs were combined and concentrated in vacuo to give an oily residue weighing 300 mg.

The sample was mixed with 5 g. of silica gel (100–200 mesh) and placed on a 100 g. silica gel column (2.5 × 45 cm.) and developed with the chloroform:isopropanol:ammonium hydroxide solvent described above. Fractions were collected, subjected to tlc analysis, and selected fractions were combined and concentrated in vacuo to a pale yellow oil weighing 0.210 g. as base. This was converted to the sulfate salt to give 0.288 g. of O-3-deoxy-4-C-methyl-3-(methylamino)-β-L-arabinopyranosyl-(1 → 6)-O-[2-amino-6-(methylamino)-6-C-methyl2,3,4,6-tetradeoxy-α-D-erythro-glucopyranosyl-(1→ 4)]-D-streptamine as the bis-base.pentasulfate. tetrahydrate.

Anal. Calcd. for: $C_{21}H_{43}N_5O_8 2\frac{1}{2} H_2SO_4 \cdot 2H_2O$: C,32.55: H,6.76; N,9.04; S,10.35. Found: C,32.49: H,6.91; N,9.36; S,9.75.

The identity of the product with the compound of the same name, designated "Component 1" in our copending application Ser. No. 550,273, was established by the following:

First, the chromatographic mobilities of the compound in two solvent systems determined by tlc analysis were identical with the chromatographic mobilities in the same systems of Component 1, which was prepared according to the process described in application Ser. No. 550,273. The chromatographic mobilities of the compound identified above and designated Example 1, Component 1 of application Ser. No. 550,273, and gentamicin $C_1$ are shown in the following table.

|  | System 1 |  | System 2 |  |
|---|---|---|---|---|
|  | $R_f$ | $R_f C_1$* | $R_f$ | $R_f C_1$* |
| Gentamicin $C_1$ | 0.39 | 1.00 | 0.70 | 1.00 |
| Component 1 | 0.30 | 0.77 | 0.63 | 0.90 |
| Example 1 | 0.30 | 0.77 | 0.63 | 0.90 |

System 1 - silica gel 60F254, lower phase of chloroform (1):methanol(1):30% ammonium hydroxide(1), plate sprayed with ninhydrin.
System 2 - Whatman No. 1 paper-solvent system same as System 1 - bioautography using *B. subtilis*.

*$R_f C_1$ - Mobility relative to gentamicin $C_1$.

Second, the mass spectrum of a sample, in the form of the free base, showed a molecular ion at 493 and fragments at 477, 476, 457, 436, 418, 405, 401, 383, 376, 366, 363, 344, 335, 321, 318, 277, 261, 160 and 157.

Third, the nuclear magnetic resonance spectrum showed signals attributable to two $NCH_3$ groups and one $CH_3CH$ group and was thus consistent with Component 1.

Fourth, a 10–20 mg. sample of the product obtained by fermentation as described above in 0.3 ml. of 6N hydrochloric acid in a 0.5 mm. capillary tube was heated in refluxing 6N hydrochloric acid for 6 hours. The mixture was allowed to stand at room temperature for 2 days, then diluted with 1.5 ml. of ethanol. The resulting clear supernatant liquid was decanted from the solid residue, and the solid was dissolved in water and chromatographed on silica gel plates using a chloroform (3):methanol(4):concentrated ammonium hydroxide (2) system. Comparative samples of authentic streptamine and deoxystreptamine were chromatographed simultaneously. The identity of the hydrolysis product with streptamine was shown by the identity of the chromatographic mobilities for these two samples (0.1) as compared with the chromatographic mobility for deoxystreptamine (0.2).

As further proof that the degradation product from the above hydrolysis was streptamine, an authentic sample of N,N-diacetylstreptamine tetraacetate was prepared by reacting 810 mg. of streptamine sulfate with 50 ml. of acetic anhydride in the presence of 500 mg. of sodium acetate. After refluxing for 1 hour, the mixture was cooled to room temperature, evaporated to dryness and extracted with chloroform/water to give 440 mg. of material having m.p. 222°–256°C. (melts with recrystallization), decomposes 334°–336°C. [Lit.-:melts partially at 250°C. with transition to long needles, melts >300°C. Peck et al. J. Am. Chem. Soc. 68, 776 (1946)].

Similar acetylation of the degradation product obtained above with 5 mg. of sodium acetate in 1 ml. of acetic anhydride afforded 5.6 mg. of material having m.p. 250°–257°C. (melts with recrystallization), decomposes at 336°–339°C. The mixed melting point between the known and the reference sample was undepressed.

Finally, vapor phase chromatographic comparisons between the N,N-diacetylstreptamine tetraacetate and the corresponding compound prepared from the degradation product were compared along with N,N-diacetyldeoxystreptamine triacetate. The streptamine derivative and the degradation sample were shown to be identical (R.T.=10.6 minutes) but different from that of N,N-diacetyldeoxystreptamine triacetate (R.T.=9.1).

Example 2

Following a procedure similar to that described in Example 1 above using 0.50 g./liter of dl-epi-inosose-2[2, 3,4,5,6-pentahydroxycyclohexanone (2,3,4,6-cis)] in three 10 liter fermentations in medium 4 plus 0.1% added phytone in the presence of *M. purpurea* ATCC 31164, and isolation of the product as before gave 0.148 g. of an oily product which, from comparison of its chromatographic mobility with known samples and from its mass spectrum, was shown to be identical with gentamicin $C_1$, namely O-3-deoxy-4-C-methyl-3-(methylamino)-$\beta$-L-arabinopyranosyl-(1 → 6)-O-[2-amino-6-(methylamino)-6-C-methyl-2,3,4,6-tetradeoxy-$\alpha$-D-erythro-glucopyranosyl-(1 → 4)]-D-2-deoxystreptamine. The mass spectrum showed a molecular ion at 477 and major fragments identical to gentamicin $C_1$ at 420, 360, 350, 347, 322, 319, 304, 160 and 157.

Example 3

Following a procedure similar to that described in Example 1 above using 0.50 g./liter of 3,4,5,6-tetrahydroxycyclohexene (3,5-cis) in three 10 liter fermentations in medium 4 plus 0.1% added phytone in the presence of *M. purpurea* ATCC 31164, and isolation of the product as before gave 0.68 g. of material which was shown, from tlc analysis and the chromatographic mobilities, to be identical with gentamicin $C_1$, $C_2$ and $C_{1a}$ mixture. Moreover, a 2 milligram sample of the material was spotted on a tlc plate along with a sample of commercial gentamicin and the plate developed with chloroform (1): methanol (1) :concentrated ammonium hydroxide (1). The resulting three bands from the experimental sample, whose chromatographic mobility values ($R_f$) corresponded identically to the three bands from the commercial gentamicin, were removed, eluted with the developing solvent and submitted for mass spectral analysis. The spectra of the first two bands having $R_f$ values of 0.37 and 0.29, respectively, were consistent with the mass spectra of gentamicin $C_1$ and gentamicin $C_2$, respectively, the mass peaks for the two samples being as follows:

Gentamicin $C_1$: $M^+477$, $M^++1$ 478, 420, 360, 350, 347, 322, 319, 304, 160, 157.
Gentamicin $C_2$: $M^+$(none), 420, 350, 346, 333, 322, 305, 304, 160, 143.

The third weaker band from the experimental sample, having an $R_f$ of 0.22, provided an insufficient sample, on elution, to permit mass spectral analysis.

Example 4 dl-Deoxyinosose [dl-2,3,4,5-tetrahydroxy-1-cyclohexanone] (500 μg./ml.) described above in Preparation 1 was incubated with mutant *M. purpurea* ATCC 31164 for 4 days in germination medium 2, and the resulting broth was found to be antibiotically active by the disc diffusion assay method against *B. subtilis* as test organism. In addition, tlc of a crude isolate from the broth showed, via bioautography using *B. subtilis* as test organism, three antibacterial components corresponding to gentamicins $C_1$, $C_2$ and $C_{1a}$ at $R_f$'s of 0.37, 0.31 and 0.26, respectively, in System 1 described in Example 1 above.

Example 5

Scyllo-inosose pentaacetate [2,3,4,5,6-pentahydroxycyclohexanone pentaacetate (2,4,6-cis)] [Kluyver et al., Rec. trav. chim. Pays-Bas 58, 956 (1939)] (500 μg./ml.) was incubated with mutant *M. purpurea* ATCC 31164 for 4 days in germination medium 2 and the resulting broth containing the streptamine analog of gentamicin was found to be antibiotically active by the disc diffusion assay method against *B. subtilis* as test organism.

Example 6 dl-Viboquercitol [dl-1,2,3,4,5p-cyclohexanepentol (1,2,4-cis)] [McCasland et al., J. Am. Chem. Soc. 75, 4020 (1953)] (500 μg./ml.) was incubated with mutant *M. purpurea* ATCC 31164 for 7 days in germination medium 2, and the resulting broth containing gentamicin was found to be antibiotically active by the disc diffusion assay method against *B. subtilis* as test organism.

Example 7 dl-2,3,4,6-Tetrahydroxy-1-cyclohexanone (2,4,6-cis) described above in Preparation 3 was incubated with mutant *M. purpurea* ATCC 31164 for four days in germination medium 2, and the resulting broth containing a mixture of O-3-deoxy-4-C-methyl-3-(methylamino)-β-L-arabinopyranosyl-(1 → 6)-O-[2-amino-6-(methylamino)-6-C-methyl-2,3,4,6-tetradeoxy-α-D-erythroglucopyranosyl-(1 → 4)]-D-5-deoxystreptamine; O-3-deoxy-4-C-methyl-3-(methylamino)-β-L-arabinopyranosyl-(1 → 6)-O-[2,6-diamino-6-C-methyl-2,3,4,6-tetradeoxy-α-D-erythroglucopyranosyl(1 → 4)]-D-5-deoxystreptamine; and O-3-deoxy-4-C-methyl-3-(methylamino)-β-L-arabinopyranosyl-(1 → 6)-O-[2,6-diamino-2,3,4,6-tetradeoxy-α-D-erythro-glucopyranosyl-(1 → 4)]-D-5-deoxystreptamine was found to be antibiotically active by the disc diffusion assay method against *B. subtilis* as test organism.

Example 8

2,4,5-Trihydroxycyclohexanone (2,4-cis) (500 μg./ml.) described above in Preparation 4 was incubated with mutant *M. purpurea* ATCC 31164 for four days in germination medium 2, and the resulting broth containing a mixture of O-3-deoxy-4-C-methyl-3-(methylamino)-β-L-arabinopyranosyl-(1 → 6)-O-[2-amino6-(methylamino)-6-C-methyl-2,3,4,6-tetradeoxy-α-D-erythro-glucopyranosyl-(1 → 4)]-D-2,5-dideoxystreptamine; O-3-deoxy-4-C-methyl-3-(methylamino)-β-L-arabinopyranosyl-(1 → 6)-O-[2,6,-diamino-6-C-methyl-2,3,4,6-tetradeoxy-α-D-erythro-glucopyranosyl-(1 → 4)]-D-2,5-dideoxystreptamine; and O-3-deoxy-4-C-methyl-3-(methylamino)-β-L-arabinopyranosyl-(1 → 6)-O-[2,6-diamino-2,3,4,6-tetradeoxy-α-D-erythro-glucopyranosyl-(1 → 4)]-D-2,5-dideoxystreptamine was found to be antibiotically active by the disc diffusion assay method against *B. subtilis* as test organism.

B. Incorporation of Aminocyclitols

Example 9

Following a procedure similar to that described in Example 1 using 0.31 g./liter of streptamine sulfate in eight 10 liter fermentations, two in production medium 4 plus 0.1% added phytone, three in production medium 4 in which tryptose was substituted for soybean meal and 3% cerelose was substituted for starch, and three in production medium 4 in which proteose peptone was substituted for soybeam meal and 3% cerelose was substituted for starch in the presence of *M. purpurea* ATCC 31164, and isolation of the product as before gave 2.4 g. of a viscous oily residue which was chromatographed on silica gel plates to give 0.56 g. of a pale yellow solid which was shown by tlc analysis to be identical with Component 1 of application Ser. No. 550,273, namely O-3-deoxy-4-C-methyl-3-(methylamino)-β-L-arabinopyranosyl-(1 → 6)-O-[2-amino-6-(methylamino)-6-C-methyl-2,3,4,6-tetradeoxy-α-D-erythro-glucopyranosyl-(1 → 4)]D-streptamine, m.p. 119°–123°C., and 0.996 g. of a pale yellow solid which was shown to be identical with "Component 2" of application Ser. No. 550,273, namely O-3-deoxy-4-C-methyl-3-(methylamino)-β-L-arabinopyranosyl-(1 → 6)-O-[2,6-diamino-6-C-methyl-2,3,4,6-tetradeoxy-α-D-erythro-glucopyranosyl-(1 → 4)]-D-streptamine, m.p. 115°–119°C., $[\alpha]_D^{25}$ (0.2% $H_2O$)=+137.1°.

A 200 mg. sample of the free base was converted to the bis-base.pentasulfate.hexahydrate to give 256 mg. of the latter, m.p. 228°–230°C.

Anal. Calcd. for $C_{20}H_{41}N_5O_8 \cdot 2\frac{1}{2}\ H_2SO_4 \cdot 3H_2O$: C,30.85; H,673; N,8.99; S,10.29. Found: C,30,45; H,6.53; N,9.03; S,10.14.

The nuclear magnetic resonance spectrum of the base was also consistent with the assigned structure and is summarized as follows:

| δ | Integration | Assignment |
|---|---|---|
| 5.82, 5.94 | 1 |  |
| 5.59 | 1 |  |
| 5.20 | 13 | $NH_2 \times 4$, $NH \times 1$, $OH \times 4$ |
| 3.0–4.6 | 13 | $-CHN-\times 5$, $-CHO-\times 6$, $-CH_2O-$ |
| 3.09 | 3 | $CH_3-N$ |
| 1.73 | 3 | $CH_3-C$ |
| 1.72 | 3 | $CH_3-CH$ |
| 1.90–2.5 | 4 | $CH_2 \times 2$ |

Example 10

Following a procedure similar to that described in Example 1 using 0.10 g./liter of 2-deoxystreptamine in a 10 liter fermentation in production medium 4 in the presence of *M. purpurea* ATCC 31164, and isolation of the product as before gave 0.51 g. of crude material which, on chromatography on silica gel, afforded, as a major component, material which was shown, by the identity of the chromatographic mobilities, to be identical with gentamicin $C_1$, namely, O-3-deoxy-4-C-methyl-3-(methylamino)-β-L-arabinopyranosyl-(1 → 6)-O-[2-amino-6-(methylamino)-6-C-methyl-2,3,4,6-tetradeoxy-α-D-erythro-glucopyranosyl-(1 → 4)]-D-2-deoxystreptamine.

Example 11

Following a procedure similar to that described in Example 1 using 0.10 g./liter of 2,5-dideoxystreptamine in two 80 liter fermentations and six 10 liter fermentations in production medium 4 in which 0.5% tryptone was substituted for soybean meal and 2% cerelose was substituted for starch in the presence of M. purpurea ATCC 31164, and isolation of the product as before gave two residues, 0.68 g. and 0.13 g., which were combined and chromatographed on silica gel plates to give three bands whose mass spectra showed them to be, respectively, Component $C_1$: O-3-deoxy-4-C-methyl-3-(methylamino)-β-L-arabinopyranosyl-(1 → 6)-O-[2-amino-6-(methylamino)-6-C-methyl-2,3,4,6-tetradeoxy-α-D-erythro-glucopyranosyl-(1 → 4)]-D-2,5-dideoxystreptamine;

Component $C_2$: O-3-deoxy-4-C-methyl-3-(methylamino)-β-L-arabinopyranosyl-(1 → 6)-O-[2,6-diamino-6-C-methyl-2,3,4,6-tetradeoxy-α-D-erythro-glucopyranosyl-(1 → 4)]-D-2,5-dideoxystreptamine and Component $C_{1a}$: O-3-deoxy-4-C-methyl-3-(methylamino)-β-L-arabinopyranosyl-(1 → 6)-O-[2,6-diamino-2,3,4,6-tetradeoxy-α-D-erythro-glucopyranosyl-(1 → 4)]-D-2,5-dideoxystreptamine.

The mass spectra for the three above-indicated components $C_1$, $C_2$ and $C_{1a}$, showed mass peaks as follows:

Component $C_1$: M⁺ 461, 404, 344, 334, 331, 306, 303, 288, 160 and 157.

Component $C_2$: M⁺ 447, 404, 334, 330, 317, 306, 288, 160 nd 143.

Component $C_{1a}$: M⁺ 433, M⁺+1 434, 404, 334, 316, 306, 303, 288, 275, 160 and 129.

The $R_f$ values, on tlc analysis on silica gel plates using the lower phase of chloroform (1):methanol(1):concentrated ammonium hydroxide (1) as developing solvent, were 0.43, 0.37 and 0.29, for components $C_1$, $C_2$ and $C_{1a}$, respectively.

Example 12

Following a procedure similar to that described in Example 1 using 0.50 g./liter of 2-amino-1,3,4,5,6-cyclohexanepentol (1,3,5-cis) in three 10 liter fermentations in production medium 4 plus 0.1% added phytone in the presence of M. purpurea ATCC 31164 and isolation of the product as before gave 214 mg. of material which was shown, from its chromatographic mobility and from its mass spectrum, to be identical with Component 1 disclosed in application Ser. No. 550,273, namely O-3-deoxy-4-C-methyl-3-(methylamino)-β-L-arabinopyranosyl-(1 → 6)-O-[2-amino-6-(methylamino)-6-C-methyl-2,3,4,6-tetradeoxy-α-D-erythro-glucopyranosyl-(1 → 4)]-D-streptamine. The mass spectrum showed mass peaks as follows: M⁺ 493, 457, 436, 383, 376, 366, 363, 346, 344, 338, 335, 321, 318, 261, 160 and 157.

Example 13

4,6-Bis(benzylideneamino)-1,3-cyclohexanediol (1,3-cis) (500 µg./ml.) described above in Preparation 2 was incubated with mutant M. purpurea ATCC 31164 for 4 days in germination medium 2, and the resulting broth containing the 2,5-dideoxystreptamine analog of gentamicin was found to be antibiotically active by the disc diffusion assay method against B. subtilis as test organism.

We claim:

1. The process for preparing aminocyclitol antibiotics of the streptamine, deoxystreptamine or dideoxystreptamine-type which comprises culturing a nutrient medium containing carbohydrates, a source of assimilable nitrogen, essential salts and a cyclitol of the 2-$R_2'$-5-$R_5'$-3,4,6-trihydroxycyclohexanone or 2-$R_2'$-5-$R_5'$-1,3,4,6-tetrahydroxycyclohexane class represented by the formula:

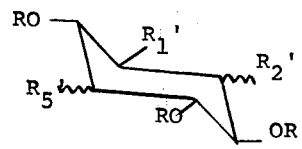

or of the 5-$R_5'$-3,4,6-trihydroxycyclohexene class represented by the formula:

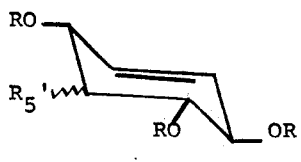

where, in either case, R is hydrogen or acetyl; $R_1'$ is oxo or hydroxy; and $R_2'$ and $R_5'$ each are hydrogen, hydroxy or OR, in the presence of microorganism mutants which are only capable of biosynthesizing antibiotics of the streptamine, deoxystreptamine or dideoxystreptamine type in the presence of the said cyclitols, and recovering said aminocyclitol antibiotics from the culture broth.

2. The process for preparing aminocyclitol antibiotics of the gentamicin-type having the formula:

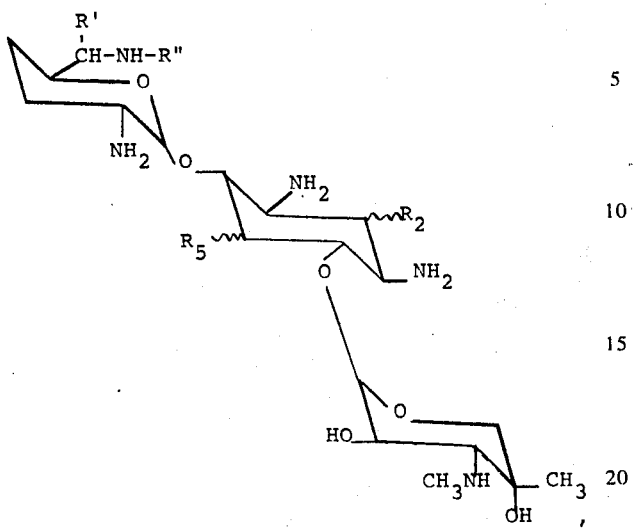

where R' and R'' each represent hydrogen or methyl, and $R_2$ and $R_5$ each represent hydrogen or hydroxy, which comprises culturing a nutrient medium containing carbohydrates, a source of assimilable nitrogen, essential salts and a cyclitol having one of the formulas:

where R' and R'' each represent hydrogen or methyl, and $R_2$ and $R_5$ each represent hydrogen or hydroxy, which comprises culturing a nutrient medium containing carbohydrates, a source of assimilable nitrogen, essential salts and an aminocyclitol having one of the formulas:

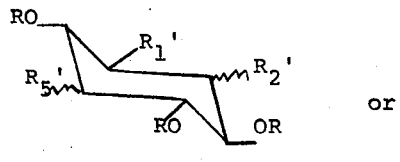 or

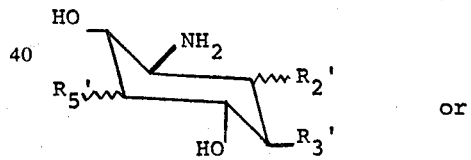 or

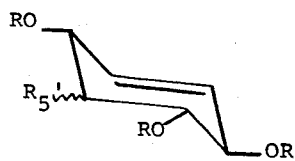

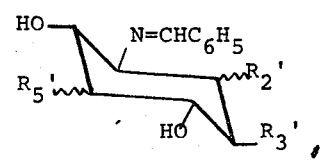

where, in either case, R is hydrogen or acetyl; $R_1'$ is oxo or hydroxy; and $R_2'$ and $R_5'$ each are hydrogen, hydroxy or OR, in the presence of *Micromonospora purpurea* ATCC 31164, which is incapable of biosynthesizing the cyclitol unit but which is capable of incorporating the cyclitol into the antibiotic molecule as an aminocyclitol unit, and recovering said aminocyclitol antibiotics from the culture broth.

3. The process for preparing aminocyclitol antibiotics of the gentamicin-type having the formula:

where, in either case, $R_2'$ and $R_5'$ are each hydrogen or hydroxy, and $R_3'$ is amino or hydroxy, in the presence of *Micromonospora purpurea* ATCC 31164, which is incapable of biosynthesizing the aminocyclitol unit but which is capable of incorporating the aminocyclitol into the antibiotic molecule as an aminocyclitol unit, and recovering said aminocyclitol antibiotics from the culture broth.

4. The process according to claim 2 for preparing O-3-deoxy-4-C-methyl-3-(methylamino)-β-L- arabinopyranosyl-(1 → 6)-O-[2-amino-6-(methylamino)-6-C-methyl-2,3,4,6-tetradeoxy-α-D-erythro-glucopyranosyl-(1 → 4)]-D-streptamine wherein the added cyclitol is scyllo-inosose.

5. The process according to claim 2 for preparing O-3-deoxy-4-C-methyl-3-(methylamino)-β-L-arabinopyranosyl-(1 → 6)-O-[2-amino-6-(methylamino)-6-C-methyl-2,3,4,6-tetradeoxy-α-D-erythro-glucopyranosyl-(1 → 4)]-D-2-deoxystreptamine wherein the added cyclitol is epi-inosose-2.

6. A process according to claim 2 for preparing gentamicin wherein the added cyclitol is 3,4,5,6-tetrahydroxycyclohexene (3,5-cis).

7. The process according to claim 2 for preparing O-3-deoxy-4-C-methyl-3-(methylamino)-β-L-arabinopyranosyl-(1 → 6)-O-[2-amino-6-(methylamino)-6-C-methyl-2,3,4,6-tetradeoxyα-D-erythro-glucopyranosyl-(1 → 4)]-D-5-deoxystreptamine; O-3-deoxy-4-C-methyl -3-(methylamino)-β-L-arabinopyranosyl-(1 → 6)-O-[2,6-diamino-6-C-methyl-2,3,4,6-tetradeoxy-α-D-erythro-glucopyranosyl-(1 → 4)]-D-5-deoxystreptamine; and O-3-deoxy-4-C-methyl-3-(methylamino)-β-L-arabinopyranosyl-(1 → 6)-O-[2,6-diamino-2,3,4,6-tetradeoxy-α-D-erythro-glucopyranosyl-(1 → 4)]D-5-deoxystreptamine wherein the added cyclitol is dl-2,3,4,6-tetrahydroxy-1-cyclohexanone (2,4,6-cis).

8. The process according to claim 2 for preparing O-3-deoxy-4-C-methyl-3-(methylamino)-β-L-arabinopyranosyl-(1 → 6)-O-[2-amino-6-(methylamino)-6-C-methyl-2,3,4,6-tetradeoxy-α-D-erythro-glucopyranosyl-(1 → 4)]-D-2,5-dideoxystreptamine; O-3-deoxy-4-C-methyl-3-(methylamino)-β-L-arabinopyranosyl-(1 → 6)-O-[2,6-diamino-6-C-methyl-2,3,4,6-tetradeoxy-α-D-erythroglucopyranosyl-(1 → 4)]-D-2,5-dideoxystreptamine; and O-3-deoxy-4-C-methyl-3-(methylamino)-β-L-arabinopyranosyl-(1 → 6)-O-[2,6-diamino-2,3,4,6-tetradeoxy-α-D-erythro-glucopyranosyl-(1 → 4)]-D-2,5-dideoxystreptamine wherein the added cyclitol is 2,4,5-trihydroxycyclohexanone (2,4-cis).

9. The process according to claim 3 for preparing O-3-deoxy-4-C-methyl-3-(methylamino)-β-L-arabinopyranosyl-(1 → 6)-O-[2-amino-6-(methylamino)-6-C-methyl-2,3,4,6-tetradeoxy-α-D-erytho-glucopyranosyl-(1 → 4)]-D-streptamine and O-3-deoxy-4-C-methyl-3-(methylamino)-β-L-arabinopyranosyl-(1 → 6)-O-[2,6-diamino-6-C-methyl-2,3,4,6-tetradeoxy-α-D-erythroglucopyranosyl-(1 → 4)]-D-streptamine wherein the added aminocyclitol is streptamine.

10. The process according to claim 3 for preparing gentamicin $C_1$, O-3-deoxy-4-C-methyl-3-(methylamino)-β-L-arabinopyranosyl-(1 → 6)-O-[2-amino-6-(methylamino)-6-C-methyl-2,3,4,6-tetradeoxy-α-D-erythro-glucopyranosyl-(1 → 4)]-D-2-deoxysteptamine. wherein the added aminocyclitol is 2-deoxystreptamine.

11. The process according to claim 3 for preparing O-3-deoxy-4-C-methyl-3-(methylamino)-β-L-arabinopyranosyl-(1 → 6)-O-[2-amino-6-(methylamino)-6-C-methyl-2,3,4,6-tetradeoxy-α-D-erythro-glucopyranosyl-(1 → 4)]-D-2,5-dideoxystreptamine, O-3-deoxy-4-C-methyl-3-(methylamino)-β-L-arabinopyranosyl-(1 → 6)-O-[2,6-diamino-6-C-methyl-2,3,4,6-tetradeoxy-α-D-erythro-glucopyranosyl-(1 → 4)]-D-2,5-dideoxystreptamine and O-3-deoxy-4-C-methyl-3-(methylamino)-β-L-arabinopyranosyl-(1 → 6)-O-[2,6-diamino-2,3,4,6-tetradeoxy-α-D-erythro-glucopyranosyl-(1 → 4)]-D-2,5-dideoxystreptamine, wherein the added aminocyclitol is 2,5-dideoxystreptamine.

12. The process according to claim 3 for preparing O-3-deoxy-4-C-methyl-3-(methylamino)-β-L-arabinopyranosyl-(1 → 6)-O-[2-amino-6-(methylamino)-6-C-methyl-2,3,4,6-tetradeoxy-α-D-erythro-glucopyranosyl-(1 → 4)]-D-streptamine wherein the added aminocyclitol is 2-amino-1,3,4,5,6-cyclohexanepentol (1,3,5,-cis).

* * * * *